(12) United States Patent
Gauvry et al.

(10) Patent No.: US 9,820,488 B2
(45) Date of Patent: Nov. 21, 2017

(54) COMPOUNDS FOR THE CONTROL OF ENDOPARASITES

(71) Applicant: Elanco Tiergesundheit AG, Indianapolis, IN (US)

(72) Inventors: Noëlle Gauvry, Kembs (FR); François Pautrat, Mulhouse (FR)

(73) Assignee: ELANCO TIERGESUNDHEIT AG, Basel (CH)

(*) Notice: Subject to any disclaimer, the term of this patent is extended or adjusted under 35 U.S.C. 154(b) by 0 days.

(21) Appl. No.: 15/030,476

(22) PCT Filed: Nov. 14, 2014

(86) PCT No.: PCT/EP2014/074622
§ 371 (c)(1),
(2) Date: Apr. 19, 2016

(87) PCT Pub. No.: WO2015/071417
PCT Pub. Date: May 21, 2015

(65) Prior Publication Data
US 2016/0251335 A1    Sep. 1, 2016

(30) Foreign Application Priority Data
Nov. 18, 2013  (CH) ...................... 1918/13

(51) Int. Cl.
| | | |
|---|---|---|
| *A01N 43/80* | (2006.01) | |
| *C07D 239/48* | (2006.01) | |
| *C07D 401/06* | (2006.01) | |
| *C07D 401/14* | (2006.01) | |
| *C07D 213/74* | (2006.01) | |
| *C07D 401/10* | (2006.01) | |
| *C07D 239/42* | (2006.01) | |
| *C07D 487/10* | (2006.01) | |
| *C07D 211/58* | (2006.01) | |
| *C07D 213/81* | (2006.01) | |
| *C07D 239/28* | (2006.01) | |

(52) U.S. Cl.
CPC ............ *A01N 43/80* (2013.01); *C07D 211/58* (2013.01); *C07D 213/74* (2013.01); *C07D 213/81* (2013.01); *C07D 239/28* (2013.01); *C07D 239/42* (2013.01); *C07D 401/06* (2013.01); *C07D 401/10* (2013.01); *C07D 401/14* (2013.01); *C07D 487/10* (2013.01)

(58) Field of Classification Search
CPC ..... A01N 43/80; C07D 239/48; C07D 401/06
USPC .......................................... 514/275; 544/323
See application file for complete search history.

(56) References Cited

FOREIGN PATENT DOCUMENTS

| | | | |
|---|---|---|---|
| CH | WO 2012163959 A1 * | 12/2012 | ............ A01N 43/80 |
| WO | 2007/038669 A2 | 4/2007 | |
| WO | 2009/071500 A2 | 6/2009 | |
| WO | 2009/152356 A2 | 12/2009 | |
| WO | WO/2010/126580 A1 | 11/2010 | |
| WO | 2011/141474 A1 | 11/2011 | |
| WO | WO/2012/163959 A1 | 12/2012 | |
| WO | WO/2013/182612 A1 | 12/2013 | |

OTHER PUBLICATIONS

Thompson, A., et al., J.Med.Chem. 2011, vol. 54, p. 6563-6585.
Valant, C., et al., J.Med.Chem. 2009, vol. 52, p. 5999-6011.

* cited by examiner

*Primary Examiner* — Kathrien Cruz
*Assistant Examiner* — Janet L Coppins
(74) *Attorney, Agent, or Firm* — Joseph M. Pletcher; Robert D. Titus

(57) ABSTRACT

The invention relates to compounds of the general formula (I) wherein the variable have the meanings as indicated in the claims, or a physiologically acceptable salt thereof. The active ingredients have advantageous pesticidal properties. They are especially suitable for controlling endoparasites in warm-blooded animals.

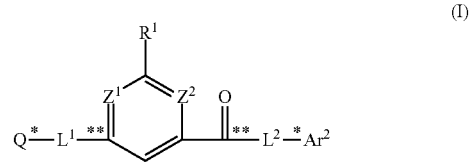

(I)

24 Claims, No Drawings

COMPOUNDS FOR THE CONTROL OF ENDOPARASITES

FIELD OF THE INVENTION

This invention relates to novel pyridinyl or pyrimidinyl compounds, processes for their manufacture, their use in the control of endoparasites in and on animals, especially productive livestock and domestic animals, and furthermore pesticidal compositions which contain one or more of these compounds.

SUMMARY OF THE INVENTION

This present invention is directed to new compounds of formula

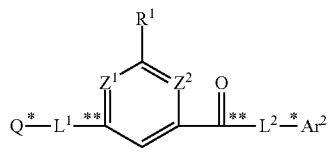

(I)

wherein $Z^1$ and $Z^2$ are each independently N or $CR^{1'}$;
$R^1$ and $R^{1'}$ are each independently of the other H, halogen, cyano, nitro, $C_1$-$C_4$-alkyl, $C_1$-$C_4$-haloalkyl, $C_1$-$C_4$-alkoxy, $C_1$-$C_3$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, halo-$C_1$-$C_4$-alkylsulfonyl, halo-$C_1$-$C_4$-alkylsulfinyl, halo-$C_1$-$C_4$-alkylsulfonylamino or benzylsulfonylamino;
Q is $Ar^1$ or —C(O)—(O)$_m$—$R^2$,
m is 0 or 1; $R^2$ is $C_1$-$C_6$-alkyl or $C_3$-$C_8$-cycloalkyl;
$Ar^1$ is (i) phenyl which is substituted by 1 to 2 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl; or is (ii) heteroaryl selected from the group consisting of 2-, 3- or 4-pyridyl and 2- or 3-thiophenyl which is each unsubstituted or substituted, for example, by methyl, ethyl, halogen, $CF_3$ or carboxy;
$Ar_2$ is phenyl which is substituted by 1 to 3 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl;
$L_1$ is a bifunctional linker radical of formula

(IIa)

(IIb)

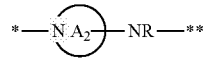

(IIc)

$L_2$ is a bifunctional linker radical of formula

(IIIa)

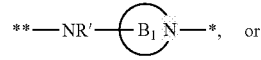

(IIIb)

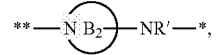

(IIIc)

A and B are each independently $C_3$-$C_8$-hetero-cycloalkylene or $C_5$-$C_{10}$-hetero-bicycloalkylene comprising two N-atoms, respectively which is each unsubstituted or substituted by $C_1$-$C_2$-alkyl;
$A_1$, $A_2$, $B_1$ and $B_2$ are each independently $C_3$-$C_8$-heterocycloalkylene comprising a N-atom, respectively;
R and R' are each independently of the other H or $C_1$-$C_4$-alkyl;
or a physiologically acceptable salt thereof.

This invention also provides a composition comprising a compound of formula (I), or a salt thereof, and at least one additional component selected from the group consisting of a surfactant, a solid diluent and a liquid diluent.

In one embodiment, this invention also provides a composition for controlling parasites, in particular endoparasites, comprising a biologically effective amount of a compound of formula (I), or a salt thereof, and at least one additional component selected from the group consisting of a surfactant, a solid diluent and a liquid diluent, said composition optionally further comprising a biologically effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl isomers.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl isomers.

"N-alkylamino", "N,N-di-alkyamino", and the like, are defined analogously to the above examples.

"Cycloalkylene" includes, for example, cyclopropylene, cyclobutylene, cyclopentylene, cyclohexylene, cycloheptylene or cyclooctylene, preferably cyclopropylene, cyclobutylene, cyclopentylene, cyclohexylene, and in particular cyclopentylene, cyclohexylene.

Examples of hetero-bicycloalkylene radicals comprising 1 or 2 heteroatoms are radicals of formula

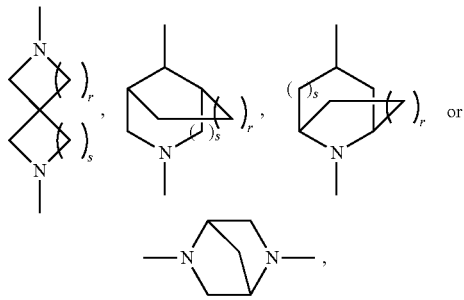

wherein r and s are each independently of the other an integer 0, 1 or 2. Examples of preferred heterobicycloalkylene radicals are spiro-diaza-$C_5$-$C_{10}$-alkylenes, such as 1,6- or 2,6-diaza spiro-[3.3] heptylene, 1,6- or 2,6-diaza spiro-[3.4] octylene or 1,7- or 2,7-diaza spiro-[4.4] nonylene.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—.

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2.

"Aromatic" indicates that each of the ring atoms is essentially in the same plane and has ap-orbital perpendicular to the ring plane, and in which (4n+2) π electrons, where n is a positive integer, are associated with the ring to comply with Hückel's rule.

In the compounds of formula (I), $R^1$ and $R^{1'}$ are each independently preferably H, halogen, cyano, $C_1$-$C_2$-haloalkyl, $C_1$-$C_2$-alkoxy, $C_1$-$C_2$-haloalkoxy, $C_1$-$C_2$-alkylthio, amino or N-mono- or N,N-di-$C_1$-$C_2$-alkylamino, more preferably H, halogen, cyano, $C_1$-$C_2$-alkoxy, $C_1$-$C_2$-alkylthio or N,N-di-$C_1$-$C_2$-alkylamino, and in particular H, cyano, methyl or methoxy. $R^1$ is preferably H, cyano, methyl or methoxy, more preferably H or cyano, and in particular H. $R^{1'}$ is preferably H, cyano, methyl or methoxy, more preferably H, cyano or methoxy, and in particular H.

According to one embodiment, $Z^1$ is N and $Z^2$ is $CR1'$, wherein for $R^{1'}$ the above-given meanings and preferences apply. Most preferably, $Z^1$ is N and $Z^2$ is CH.

According to a further embodiment, $Z^1$ and $Z^2$ are both N.

According to still another embodiment, $Z^1$ is $CR^{1'}$ and $Z^2$ is N, wherein for $R^{1'}$ the above-given meanings and preferences apply. Most preferably, $Z^1$ is CH and $Z^2$ is N.

According to still another embodiment, $Z^1$ and $Z^2$ are each independently $CR^{1'}$, wherein for $R^{1'}$ the above-given meanings and preferences apply, in particular both CH.

$Ar^1$ as phenyl is preferably phenyl which is substituted by 1 or 2 same or different substituents selected from the group consisting of halogen, cyano, nitro, $C_1$-$C_2$-alkyl, $C_1$-$C_2$-haloalkyl, $C_1$-$C_2$-alkoxy or $C_1$-$C_2$-haloalkoxyl. A especially preferred phenyl radical $Ar_1$ is phenyl which is substituted by 1 or 2 same or different radicals selected from the group consisting of halogen, cyano and $C_1$-$C_2$-haloalkyl, in particular chlorine, fluorine, cyano or $CF_3$. A particularly preferred phenyl radical $Ar^1$ is phenyl mono-substituted by $CF_3$, especially 4-$CF_3$-phenyl.

A preferred heteroaryl radical $Ar^1$ is 2-, 3- or 4-pyridyl which is unsubstituted or substituted, for example, by methyl, ethyl, halogen, $CF_3$ or carboxy. A particularly preferred heteroaryl radical $Ar^1$ is 2- or 3-pyridyl which is unsubstituted or substituted by halogen or $CF_3$, especially 5-$CF_3$-pyrid-2-yl or 6-$CF_3$-pyrid-3-yl.

$R^2$ is preferably $C_1$-$C_4$-alkyl or $C_3$-$C_6$-cycloalkyl, in particular tert.-butyl, cyclopropyl, cyclobutyl, cyclopentyl or cyclohexyl, in particular tert.-butyl or cyclopropyl, especially tert.-butyl.

A preferred radical Q is phenyl which is substituted by 1 or 2 same or different radicals selected from the group consisting of chlorine, fluorine, cyano or $CF_3$; 2- or 3-pyridyl which is unsubstituted or substituted by halogen or $CF_3$; or is —C(O)—(O)$_{0-1}$—$R^2$, wherein $R^2$ is $C_1$-$C_4$-alkyl or $C_3$-$C_6$-cycloalkyl. A particularly preferred radical Q is 4-$CF_3$-phenyl, 5-$CF_3$-pyrid-2-yl, 6-$CF_3$-pyrid-3-yl, —C(O)—O-tert.-butyl or —C(O)-cyclopropyl.

$Ar^2$ as phenyl is preferably phenyl which is substituted by 1 or 2 same or different substituents selected from the group consisting of halogen, cyano, nitro, $C_1$-$C_4$-alkyl, $C_1$-$C_2$-haloalkyl, $C_1$-$C_2$-alkoxy, $C_1$-$C_2$-haloalkoxyl, $C_1$-$C_2$-alkylthio, $C_1$-$C_2$-haloalkylthio, $C_1$-$C_2$-alkylsulfonyl, halo-$C_1$-$C_2$-alkylsulfonyl, amino, N-mono- and N,N-di-$C_1$-$C_4$-alkylamino, aminosulfonyl and $C_1$-$C_2$-alkylaminosulfonyl. An even more preferred phenyl radical $Ar^2$ is phenyl which is substituted by 1 or 2 same or different radicals selected from the group consisting of halogen, cyano, nitro, $C_1$-$C_4$-alkyl, $C_1$-$C_2$-haloalkyl, $C_1$-$C_2$-alkoxy, $C_1$-$C_2$-haloalkoxyl, $C_1$-$C_2$-haloalkylthio, $C_1$-$C_2$-alkylsulfonyl, halo-$C_1$-$C_2$-alkylsulfonyl, amino and $C_1$-$C_2$-alkylaminosulfonyl. A particularly preferred phenyl radical $Ar^2$ is phenyl which is substituted by 1 or 2 same or different radicals selected from the group consisting of halogen, cyano, nitro, $C_1$-$C_2$-haloalkyl, $C_1$-$C_2$-haloalkoxyl or $C_1$-$C_2$-haloalkylthio. An especially preferred phenyl radical $Ar^2$ is phenyl which is substituted by 2 same or different radicals selected from the group consisting of fluorine, cyano, nitro and $CF_3$. Examples of specifically preferred radicals $Ar^2$ are 4-nitro-3-$CF_3$-phenyl, 4-cyano-2-$CF_3$-phenyl, 4-cyano-3-$CF_3$-phenyl, 3,4-di-$CF_3$-phenyl, 4-$CF_3$-3-fluorophenyl, 3-$CF_3$-4-fluorophenyl, in particular 4-cyano-3-$CF_3$-phenyl.

The radicals $L^1$ and $L^2$ may be identical or different, in particular different.

Concerning the radical $L^1$ the following preferences apply:

The variable A is preferably an unsubstituted hetero-cycloalkylene or hetero-bicycloalkylene radical, and especially $C_3$-$C_6$-hetero-cycloalkylene or $C_5$-$C_8$-hetero-bicycloalkylene comprising two N-atoms, respectively.

A preferred linker $L^1$ of formula (IIa) is a radical

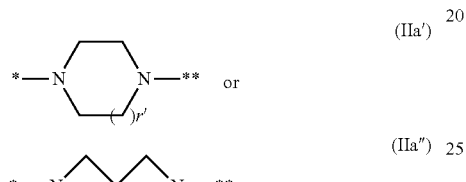

(IIa')

(IIa'')

wherein s and r are each independently an integer 1 or 2, and r' is an integer 0, 1 or 2; in the above formulae, one of s and r is preferably 1 and the other one is 1 or 2, and r' is preferably 1 or 2, in particular 1.

Examples of bifunctional linkers of formula (IIa) are

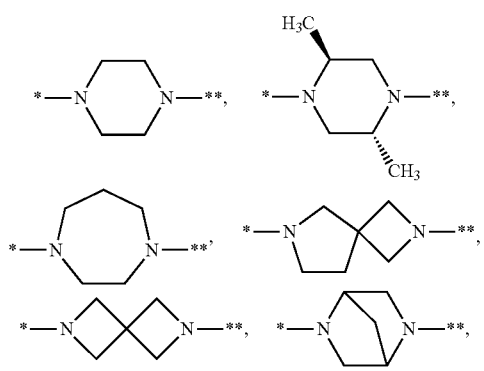

in particular

or especially

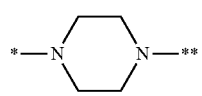

(piperazine 1,4-diyl).

A preferred bifunctional linker of formula (IIb) is a radical

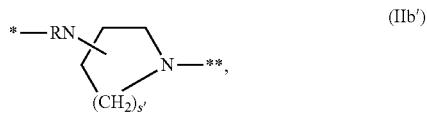

(IIb')

wherein s' is an integer 0, 1 or 2 and R is H or methyl, in particular H.

Examples of bifunctional linkers of formula (IIb) are

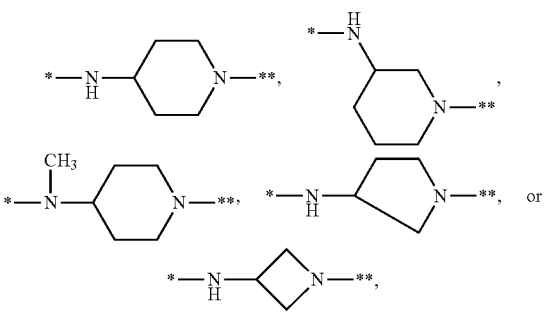

in particular the radical

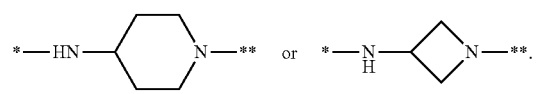

A preferred bifunctional linker of formula (IIc) is a radical

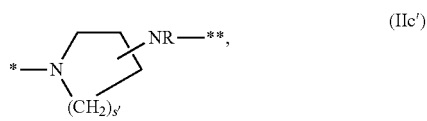

(IIc')

wherein s' is an integer 0, 1 or 2, in particular 1 or 2 and R is H or methyl.

Examples of suitable bifunctional linkers of formula (IIc) are a radical

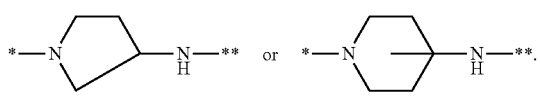

A particularly preferred radical $L_1$ is the radical

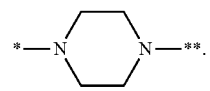

Concerning the radical $L_2$ the following preferences apply:

B is preferably an unsubstituted hetero-cycloalkylene or hetero-bicycloalkylene radical, and especially $C_3$-$C_6$-hetero-cycloalkylene, in particular $C_3$-$C_4$-hetero-cycloalkylene, comprising two N-atoms.

A preferred bifunctional linker $L^2$ of formula (IIIa) is a radical of formula

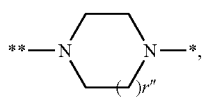
(IIIa')

wherein r" is 0 or 1, in particular the radical

A preferred bifunctional linker $L^2$ of formula (IIIb) is a radical of formula

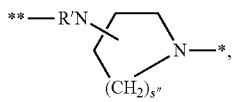
(IIIb')

wherein s" is an integer 0, 1 or 2, and R' is H or methyl, in particular H; especially a radical

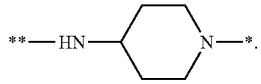

A preferred bifunctional linker $L^2$ of formula (IIIc) is a radical of formula

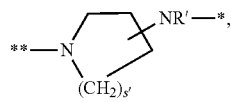

wherein s' is an integer 0, 1 or 2, in particular 1 or 2, and R' is H or methyl, in particular H.

Examples are a radical

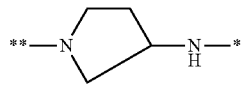

or especially

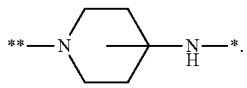

Examples of particular preferred radicals $L^2$ are a radical

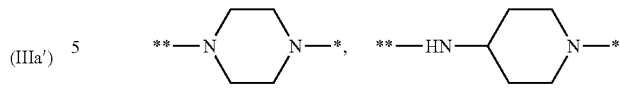

or especially.

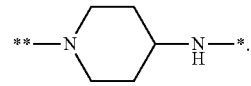

One preferred group of compounds according to the invention is of formula

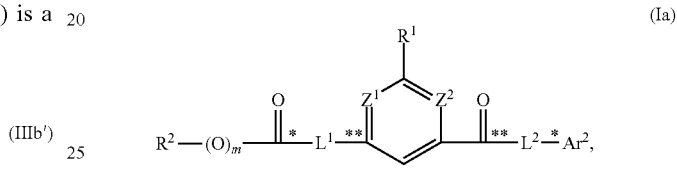
(Ia)

wherein for $R^1$, $R^2$, m, $L^1$, $L^2$, $Z^1$, $Z^2$ and $Ar^2$ each the above given meanings and preferences apply.

A further preferred group of compounds according to present invention is of formula

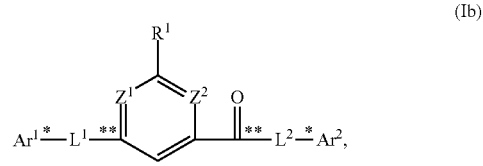
(Ib)

wherein for $R^1$, $Ar^1$, $Ar^2$, $L^1$, $L^2$, $Z^1$ and $Z^2$ each the above given meanings and preferences apply, or a physiologically acceptable salt thereof.

A preferred embodiment of the present invention relates to a compound of formula (I) above, wherein $Z^1$ and $Z^2$ are each independently N or $CR^{1'}$;
$R^1$ and $R^{1'}$ are each independently of the other H, cyano, methyl or methoxy, in particular H;
Q is phenyl which is substituted by 1 or 2 same or different radicals selected from the group consisting of chlorine, fluorine, cyano or $CF_3$; 2- or 3-pyridyl which is unsubstituted or substituted by halogen or $CF_3$; or is —C(O)—$(O)_{0-1}$—$R^2$, wherein $R^2$ is $C_1$-$C_4$-alkyl or $C_3$-$C_6$-cycloalkyl;
$Ar^2$ is phenyl which is substituted by 2 same or different radicals selected from the group consisting of fluorine, cyano, nitro and $CF_3$;
$L^1$ is a radical

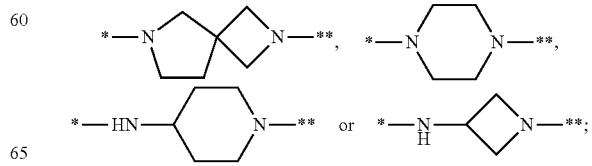

and

L² is a radical

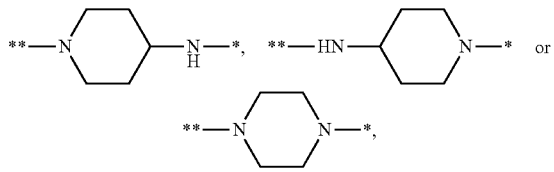

or a physiologically acceptable salt thereof.

A further preferred embodiment of the present invention concerns a compound of formula

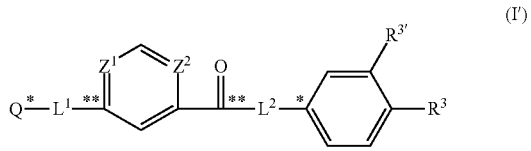

(I')

wherein Q is 4-CF$_3$-phenyl, 5-CF$_3$-pyrid-2-yl, 6-CF$_3$-pyrid-3-yl, —C(O)—O-tert.-butyl or —C(O)— cyclopropyl;

Z$^1$ is N or CH, in particular N;

Z$^2$ is N or CH, in particular CH;

L$^1$ is a radical,

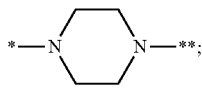

L$^2$ is a radical

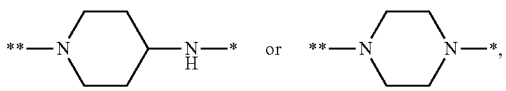

in particular

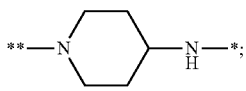

R$^3$ is CF$_3$; and R$^{3'}$ is cyano or nitro, in particular cyano, or a physiologically acceptable salt thereof.

The compounds of formula (I) may be prepared, for example, by reacting a compound of formula

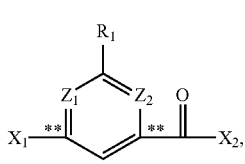

(IV)

wherein R$_1$, Z$_1$ and Z$_2$ are each as defined above and X$_1$ and X$_2$ are each independently a leaving group, for example halogen, in particular chlorine, successively with a compound each of formulae Q-L$_1$-H           (Va), and H-L$_2$-Ar$_2$      (Vb)

Wherein Q, Ar$_2$, L$_1$ and L$_2$ are each as defined above, in a manner known per se, in particular in a medium which is suitable for aromatic nucleophilic substitution of a pyridine or pyrimidine of the above formula (IV). The reaction conditions vary depending on the reactivity of the compound of formula (Va) or (Vb) employed. A compound of formula (Va) or (Vb) with a terminal hydroxyl or thiol group reacts more readily with a compound of formula (IV)—for example in an aprotic dipolar solvent at room temperature—than a compound of formula (Va) or (Vb) with a terminal primary or secondary amino group, which is preferably reacted in dipolar aprotic solvents at higher temperatures such as 70 to 120° C., optionally in the presence of a catalyst such as Pd(OAc)$_2$, RuPhos and the like. Specific examples of these aromatic nucleophilic substitution reactions of halopyridines and halopyrimidines are known, for example, from J. Med. Chem. 2011, Vol 54, p. 6563-6585, J. Med. Chem. 2009, Vol 52, p. 5999-6011, or Chem. Science 2011, Vol. 2, p. 57-68.

The compounds of formula (IV) are known or can be obtained by methods known per se.

The compounds of formula (Va) and (Vb) likewise may be obtained by methods known per se, for example by aromatic nucleophilic substitution of a halogenated compound Ar$_1$ or Ar$_2$ with a compound H-L$_1$-H or H-L$_2$H.

Salts of compounds I may be produced in known manner. Acid addition salts of compounds I, for example, are obtainable by treatment with a suitable acid or a suitable ion exchange reagent, and salts with bases are obtainable by treatment with a suitable base or a suitable ion exchange reagent.

Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of salts.

Compounds I can also be obtained in the form of their hydrates and/or also can include other solvents, used for example where necessary for the crystallisation of compounds present in solid form.

The compounds of formula I may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds of formula (I), which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers, that are obtainable accordingly, into the pure isomers, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, whereby only one enantiomer is complexed.

The compounds (I) according to the invention are notable for their broad activity spectrum and are valuable active ingredients for use in pest control, including in particular the control of endo- and ecto-parasites, especially helminths, in and on warm-blooded animals, especially livestock and domestic animals, whilst being well-tolerated by warm-blooded animals and fish.

In the context of the present invention, ectoparasites are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (Nematocera), such as Culicidae, Simuliidae, Psychodidae, but also blood-sucking parasites, for example fleas, such as *Ctenocephalides felis* and *Ctenocephalides canis* (cat and dog fleas), *Xenopsylla cheopis, Pulex irritans, Dermatophilus penetrans*, lice, such as *Damalina ovis, Pediculus humanis*, biting flies and horse-flies (Tabanidae), *Haematopota* spp. such as *Haematopota pluvialis, Tabanidea* spp. such as *Tabanus nigrovittatus*, Chrysopsinae spp. such as *Chrysops caecutiens*, tsetse flies, such as species of *Glossinia*, biting insects, particularly cockroaches, such as *Blatella germanica, Blatta orientalis, Periplaneta americana*, mites, such as *Dermanyssus gallinae, Sarcoptes scabiei, Psoroptes ovis* and *Psorergates* spp. and last but not least ticks. The latter belong to the order Acarina. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds of formula (I) according to the invention are also active against all or individual development stages of animal pests showing normal sensitivity, as well as those showing resistance, such as insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds (I) can also be used against hygiene pests, especially of the order Diptera of the families Sarcophagidae, Anophilidae and Culicidae; the orders Orthoptera, Dictyoptera (e.g. the family Blattidae) and Hymenoptera (e.g. the family Formicidae).

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs or exotic birds, in particular sheep or especially cattle. Typical nematodes of this indication are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris, Dirofilaria, Acanthocheilonema* and *Parascaris*. The trematodes include, in particular, the family of Fasciolideae, especially *Fasciola hepatica*.

It could also be shown surprisingly and unexpectedly that the compounds of formula (I) have exceptionally high efficacy against nematodes that are resistant to many active substances. This can be demonstrated in vitro by the LDA test and in vivo for example in Mongolian gerbils. It was shown that amounts of active substance which kill sensitive strains of *Haemonchus contortus* or *Trichostrongylus colubriformis*, are also sufficiently effective at controlling corresponding strains that are resistant to benzimidazoles or levamisole.

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filariidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula (I) are highly effective against these parasites.

The pests which may be controlled by the compounds of formula I also include those from the class of Cestoda (tapeworms), e.g. the families Mesocestoidae, especially of the genus *Mesocestoides*, in particular *M. lineatus*; Dilepidide, especially *Dipylidium caninum, Joyeuxiella* spp., in particular *Joyeuxiella pasquali*, and *Diplopylidium* spp., and Taeniidae, especially *Taenia pisiformis, Taenia cervi, Taenia ovis, Taneia hydatigena, Taenia multiceps, Taenia taeniaeformis, Taenia serialis*, and *Echinocuccus* spp., most preferably *Taneia hydatigena, Taenia ovis, Taenia multiceps, Taenia serialis; Echinocuccus granulosus* and *Echinococcus granulosus* and *Echinococcus multilocularis*, as well as *Multiceps multiceps*.

Most particularly, *Taenia hydatigena, T. pisiformis, T. ovis, T. taeniaeformis, Multiceps multiceps, Joyeuxiella pasquali, Dipylidium caninum, Mesocestoides* spp., *Echinococcus granulosus* and *E. multilocularis* are controlled on or in dogs and cats simultaneously with *Dirofilaria* ssp., *Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula (I) are suitable for the control of human pathogenic parasites. Of these, typical representatives that appear in the digestive tract are those of the species *Ancylostoma, Necator, Ascaris, Strongyloides, Trichinella, Capillaria, Trichuris* and *Enterobius*. The compounds of the present invention are also effective against parasites of the species *Wuchereria, Brugia, Onchocerca* and *Loa* from the family of Filariidae, which appear in the blood, in the tissue and in various organs, and also against *Dracunculus* and parasites of the species *Strongyloides* and *Trichinella*, which infect the gastrointestinal tract in particular.

The good pesticidal activity of the compounds of formula (I) according to the invention corresponds to a mortality rate of at least 50-60% of the pests mentioned. In particular, the compounds of formula (I) are notable for the exceptionally long duration of efficacy.

The compounds of formula (I) are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula (I), or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, microcapsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5-200 ppm).

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stages of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I).

Suitable partners in the mixture may be biocides, e.g. the insecticides and acaricides with a varying mechanism of activity, which are known to the person skilled in the art, e.g. chitin synthesis inhibitors, growth regulators; active ingredients which act as juvenile hormones; active ingredients which act as adulticides; broad-band insecticides, broad-band acaricides and nematicides; and also the well-known anthelminthics and insect- and/or acarid-deterring substances, repellents, detachers and synergists.

Non-limitative examples of suitable insecticides and acaricides are mentioned in WO 2009/071500, compounds Nos. 1-284 on pages 18-21.

Non-limitative examples of suitable anthelminthics are mentioned in WO 2009/071500, compounds (A1)-(A31) on page 21.

Non-limitative examples of suitable repellents and detachers are mentioned in WO 2009/071500, compounds (R1)-(R3) on page 21 and 22.

Non-limitative examples of suitable synergists are mentioned in WO 2009/071500, compounds (S1)-(S3) on page 22.

Accordingly, a further essential aspect of the present invention relates to combination preparations for the control of parasites on warm-blooded animals, characterised in that they contain, in addition to a compound of formula (I), at least one further active ingredient having the same or different sphere of activity and at least one physiologically acceptable carrier. The present invention is not restricted to two-fold combinations.

In one embodiment of the invention, the compound of formula (I) is used in combination with one or more further anthelmintic agents. Such a combination may reduce further the likelihood of resistance developing. Suitable further anthelmintic agents include.

The Examples further illustrate the invention. Characterization data reported thereafter in the last column of Tables 1 and 2 is done using a Waters Autopurification (HPLC/MS) system with a reversed phase column (XTerra®, MS C18 5 μm, 50×4.6 mm). The samples are characterized by m/z and retention time. The retention times relate in each case to the use of a solvent system comprising two different solvents, solvent A: $H_2O+0.01\%$ HCOOH, and solvent B: $CH_3CN+0.01\%$ HCOOH). Said two solvents A and B are employed at a flow rate of 2.00 ml/min with a time-dependent gradient as given in the Table:

| Time [min] | A [%] | B [%] |
|---|---|---|
| 0 | 70.0 | 30.0 |
| 0.5 | 70.0 | 30.0 |
| 0.75 | 55.1 | 44.9 |
| 1 | 41.2 | 58.8 |
| 1.25 | 30.3 | 69.7 |
| 1.5 | 21.4 | 78.6 |
| 1.75 | 13.8 | 86.2 |
| 2 | 9.0 | 91.0 |
| 2.25 | 6.0 | 94.0 |
| 2.5 | 5.0 | 95.0 |
| 2.8 | 5.0 | 95.0 |
| 2.9 | 70.0 | 30.0 |
| 3.0 | 70.0 | 30.0 |

Example 1 (No. 32 in the Table 2 Below)

At 0° C. under nitrogen, 366 mg of commercially available 2-chloropyridine-4-carbonyl chloride dissolved in 2 ml of dichloromethane were added dropwise to a solution of 530 mg of commercially available 4-(1-piperazinyl)-2-trifluoromethylbenzonitrile in 5 ml of dichloromethane and 630 mg of $Et_3N$. The reaction mixture was stirred overnight at room temperature, poured over a stirred mixture of 100 ml EtOAc and 40 ml of water. The aqueous layer was extracted with EtOAc. The combined organic layers were washed with brine, dried over $MgSO_4$, filtered, concentrated under vacuum and purified by column chromatography on silica gel to isolate 620 mg of 4-{4-[(2-chloropyridin-4-yl)carbonyl]piperazin-1-yl}-2-(trifluoromethyl)benzonitrile. 99 mg of this material were then added to a degased mixture of 85 mg of commercially available 1-(4-trifluoromethylphenyl)piperazine, 6 mg of $Pd(OAc)_2$, 23 mg of RuPhos, 163 mg of $Cs_2CO_3$, and 1.5 ml of tert-Butanol then, heated to 85° C. overnight. The reaction mixture was then poured at room temperature over a stirred mixture of 50 ml of EtOAc and 10 ml of water. The aqueous layer was extracted with 10 ml EtOAc. The combined organic layers were washed with brine, dried over $MgSO_4$, filtered, concentrated under vacuum and purified by column chromatography to isolate 60 mg of compound No. 32 in Table 2.

The substances as shown in the following Tables 1 and 2 are prepared analogously to the above-described methods.

TABLE 1

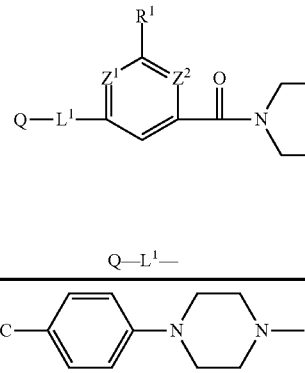

| No. | Q—L¹— | Z¹ | Z² | R¹ | Retention Time (min.)/ [MH]+ |
|---|---|---|---|---|---|
| 1 | 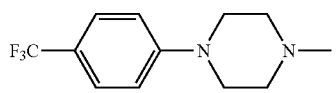 | N | N | H | 1.78/604.1 |
| 2 | 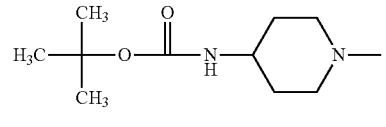 | N | CH | H | 1.76/603.1 |
| 3 | 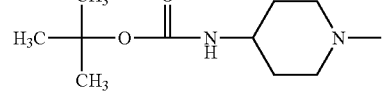 | CH | N | H | 1.24/573.1 |
| 4 | 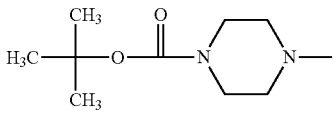 | N | CH | H | 1.33/573.0 |
| 5 |  | N | CH | H | 1.51/559.0 |

TABLE 1-continued

| No. | Q—L¹— | Z¹ | Z² | R¹ | Retention Time (min.)/ [MH]+ |
|---|---|---|---|---|---|
| 6 | (CH₃)₃C-O-C(O)-N(piperazine)N-CH₃ | N | N | H | 1.56/560.0 |
| 7 | (CH₃)₃C-O-C(O)-NH-(piperidine)N-CH₃ | N | N | H | 1.48/574.0 |
| 8 | F₃C-C₆H₄-NH-(piperidine)N-CH₃ | N | N | H | 1.75/618.0 |
| 9 | F₃C-C₆H₄-N(piperazine)N-CH₃ | CH | N | H | 1.37/603.0 |
| 10 | (CH₃)₃C-O-C(O)-N(piperazine)N-CH₃ | CH | N | H | 1.24/559.0 |
| 11 | 5-CF₃-pyridin-2-yl-N(piperazine)N-CH₃ | N | CH | H | 1.63/603.9 |
| 12 | (CH₃)₃C-O-C(O)-NH-(piperidine)N-CH₃ | CH | CH | H | 1.67/572.0 |
| 13 | F₃C-C₆H₄-N(piperazine)N-CH₃ | CH | CH | H | 2.00/602.2 |
| 14 | 5-CF₃-pyridin-2-yl-NH-(piperidine)N-CH₃ | N | CH | H | 1.42/617.9 |
| 15 | (CH₃)₃C-O-C(O)-N(piperazine)N-CH₃ | CH | CH | H | 1.78/558.0 |
| 16 | F₃C-C₆H₄-N(piperazine)N-CH₃ | C(OCH₃) | CH | H | 2.00/632.1 |
| 17 | cyclopropyl-C(O)-N(piperazine)N-CH₃ | N | CH | H | 1.22/527.0 |

TABLE 1-continued

| No. | Q—L¹— | Z¹ | Z² | R¹ | Retention Time (min.)/ [MH]+ |
|---|---|---|---|---|---|
| 18 | F₃C-pyridine-N(piperazine)N-methyl | CH | N | H | 1.28/604.1 |
| 19 | F₃C-phenyl-N(piperazine)N-methyl | CH | CH | CN | 1.99/627.1 |
| 20 | F₃C-phenyl-N(piperazine)N-methyl | CH | C(OCH₃) | H | 1.98/632.1 |
| 21 | cyclopropyl-C(O)-N(piperazine)N-methyl | C(OCH₃) | CH | H | 1.48/556.2 |
| 22 | F₃C-pyridine-NH-piperidine-N-methyl | CH | N | H | 1.28/618.2 |
| 23 | F₃C-phenyl-NH-azetidine-N-methyl | CH | CH | H | 1.93/(586.3) |
| 24 | cyclopropyl-C(O)-N(piperazine)N-methyl | CH | CH | H | 1.5/526 |
| 25 | (H₃C)₃C-O-C(O)-NH-azetidine-N-methyl | CH | CH | H | 1.71/(542.4) |
| 26 | cyclopropyl-C(O)-N(2,6-diazaspiro)N-methyl | CH | CH | H | 1.52/(550.4) |
| 27 | cyclopropyl-C(O)-NH-azetidine-N-methyl | CH | CH | H | 1.5/512 |
| 28 | F₃C-phenyl-N(2,6-diazaspiro)N-methyl | CH | CH | H | 2.15/(626.6) |
| 29 | (H₃C)₃C-O-C(O)-N(2,6-diazaspiro)N-methyl | CH | CH | H | 1.84/(582.5) |

TABLE 1-continued

Structure: Q—L¹—[Z¹=Z²(R¹)]—C(=O)—N(piperidine)—NH—[phenyl(CF₃)(CN)]

| No. | Q—L¹— | Z¹ | Z² | R¹ | Retention Time (min.)/[MH]+ |
|---|---|---|---|---|---|
| 30 | 4-(trifluoromethyl)phenyl-N(piperazine)N-methyl | C(CN) | CH | H | 2.01/(625.1) |
| 30a | 3-(trifluoromethyl)phenyl-N(piperazine)N-methyl | N | CH | H | 1.82/(602.9) |

TABLE 2

Structure: Q—L¹—[Z¹=Z²]—C(=O)—N(piperazine)N—[phenyl(CF₃)(CN)]

| No. | Q—L¹ | Z₁ | Z₂ | Retention Time (min.)/[MH]+ |
|---|---|---|---|---|
| 31 | 4-(trifluoromethyl)phenyl-N(piperazine)N-methyl | N | N | 1.80/590.0 |
| 32 | 4-(trifluoromethyl)phenyl-N(piperazine)N-methyl | N | CH | 1.78/589.0 |
| 33 | 4-cyano-3-(trifluoromethyl)phenyl-NH-(1-methylpiperidin-4-yl) | N | CH | —/628.2 |
| 34 | (CH₃)₃C-O-C(=O)-NH-(1-methylpiperidin-4-yl) | N | CH | 1.37/559.0 |
| 35 | (CH₃)₃C-O-C(=O)-NH-(1-methylpiperidin-4-yl) | CH | N | 1.53/559.0 |
| 36 | (CH₃)₃C-O-C(=O)-N(piperazine)N-methyl | CH | N | 1.24/544.9 |
| 37 | (CH₃)₃C-O-C(=O)-N(piperazine)N-methyl | N | CH | 1.55/545.0 |
| 38 | 4-(trifluoromethyl)phenyl-N(piperazine)N-methyl | CH | N | 1.37/589.0 |
| 39 | 4-(trifluoromethyl)phenyl-NH-(1-methylpiperidin-4-yl) | CH | N | —/603.2 |
| 40 | (CH₃)₃C-O-C(=O)-N(piperazine)N-methyl | N | N | 1.58/545.9 |
| 41 | (CH₃)₃C-O-C(=O)-NH-(1-methylpiperidin-4-yl) | N | N | 1.50/559.9 |
| 42 | 4-(trifluoromethyl)phenyl-NH-(1-methylpiperidin-4-yl) | N | N | 1.77/603.9 |

The following molecules are prepared in analogues manner:

| No. | Chemical Formula | Retention Time (min.)/ [MH]+ |
|---|---|---|
| 43 | F3C-[phenyl]-N[piperazine]N-[pyrimidine]-C(O)-N[piperidine]-NH-[phenyl(CF3)(NO2)] | 1.83/624.0 |
| 44 | F3C-[phenyl]-N[piperazine]N-[pyridine]-C(O)-N[piperidine]-NH-[phenyl(CF3)(NO2)] | 1.80/623.0 |
| 45 | tBu-O-C(O)-NH-[piperidine]-N-[pyridine]-C(O)-NH-[piperidine]-N-[phenyl(CF3)(CN)] | 1.41/573.1 |
| 46 | F3C-[pyridine]-N[piperazine]N-[pyridine]-C(O)-N[piperidine]-NH-[phenyl(CF3)(CN)] | 1.70/603.9 |

The anthelmintic potential of the novel compound is assessed in the following tests:

Gastro-Intestinal Larval Development Assay

Freshly harvested and cleaned nematode eggs are used to seed a suitably formatted well plate containing the test substances to be evaluated for antiparasitic activity and media allowing the full development of eggs through to 3rd instar larvae. The plates are incubated for 6 days at 25° C. and 60% relative humidity. Egg-hatching and ensuing larval development are recorded to identify a possible nematodicidal activity. Efficacy is expressed in percent reduced egg hatch, reduced development of L3, or paralysis & death of larvae at any stage. Compounds Nos. 1, 2, 3, 4, 5, 6, 7, 8, 9, 10, 11, 12, 13, 14, 15, 17, 18, 23, 24, 25, 26, 27, 29, 31, 32, 34, 35, 36, 37, 38, 39, 40, 41, 42, 43, 44 and 46 reached ≥60% efficacy at 10 ppm, and are therefore considered active.

Gastro-Intestinal Worms in Gerbil

Gerbils are artificially infected by gavage with ca. 2000 third instar larvae each of *T. colubriformis* (Tc) and *H. contortus* (Hc) 7, respectively 6, days before treatment. Treatment is performed orally (p.o.) with the formulated test compound. 3 days after treatment, gerbils are euthanised and dissected to recover *H. contortus* from stomach and *T. colubriformis* from upper part of midgut.

Efficacy is expressed as a percentage reduction in worm numbers in comparison with a placebo treated group, using the Abbot's formula. Compounds Nos. 1, 2, 4, 5, 6, 8, 11, 12, 13, 15, 23, 25, 31, 32, 34, 42, 43, and 44 showed an efficacy above 80% against Hc in gerbils at least at 10 mg/kg p.o., and compounds Nos 2, 11, 13, 43, and 44 showed an efficacy above 80% against Tc in gerbils at least at 10 mg/kg p.o. and are therefore considered active.

active.

*Dirofilaria immitis* Microfilaria Assay

Freshly harvested and cleaned *Dirofilaria immitis* microfilariae are prepared from blood from donor animals dogs. The microfilariae are then distributed in formatted microplates containing the test substances to be evaluated for antiparasitic activity. The plates are incubated for 48 hours at 25° C. and 60% relative humidity (RH). Motility of microfilariae is then recorded to determine efficacy. Efficacy is expressed in percent reduced motility as compared to the control and standards. Compounds Nos. 1-46 each showed an efficacy above 50% at 10 ppm, and are therefore considered active.

*Acanthocheilonema viteae* in Gerbil.

Gerbils are artificially infected with 80 L3 larvae of *A. viteae* by subcutaneous injection. Treatment by gavage with the formulated test compounds occurs consecutively day 5 to day 9 after infection. Eighty-four days after infection, gerbils are bled for counting circulating microfilariae, using a Fuchs-Rosenthal counting chamber and microscope. Only test groups with an average of circulating microfilariae at least 50% lower than in the placebo treated group are fully dissected to recover adult worms. Efficacy is expressed as a % reduction in worm numbers in comparison with the placebo treated group, using the Abbot's formula. Compound No. 1 showed an efficacy above 80% at 3 mg/kg.

The invention claimed is:

1. A compound of formula

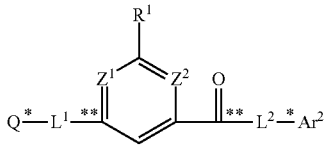
(I)

wherein $Z^1$ and $Z^2$ are each independently N or $CR^{1'}$;
$R^1$ and $R^{1'}$ are each independently of the other H, halogen, cyano, nitro, $C_1$-$C_4$-alkyl, $C_1$-$C_4$-haloalkyl, $C_1$-$C_4$-alkoxy, $C_1$-$C_3$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, halo-$C_1$-$C_4$-alkylsulfonyl, halo-$C_1$-$C_4$-alkylsulfinyl, halo-$C_1$-$C_4$-alkylsulfonylamino or benzylsulfonylamino;
Q is $Ar^1$ or —C(O)—(O)$_m$—$R^2$;
m is 0 or 1; $R^2$ is $C_1$-$C_6$-alkyl or $C_3$-$C_8$-cycloalkyl;
$Ar^1$ is (i) phenyl which is substituted by 1 to 2 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl; or is (ii) heteroaryl selected from the group consisting of 2-, 3- or 4-pyridyl and 2- or 3-thiophenyl which is each unsubstituted or substituted by methyl, ethyl, halogen, $CF_3$ or carboxy;
$Ar^2$ is phenyl which is substituted by 1 to 3 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl;
$L_1$ is a bifunctional linker radical of formula

(IIa)

(IIb)

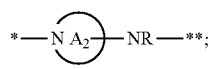
(IIc)

$L_2$ is a bifunctional linker radical of formula

(IIIa)

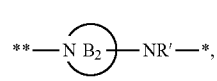
(IIIc)

A and B are each independently $C_3$-$C_8$-hetero-cycloalkylene or $C_5$-$C_{10}$-hetero-bicycloalkylene comprising two N-atoms, respectively which is each unsubstituted or substituted by $C_1$-$C_2$-alkyl;
$A_1$, $A_2$, and $B_2$ are each independently $C_3$-$C_8$-heterocycloalkylene comprising a N-atom, respectively;
R and R' are each independently of the other H or $C_1$-$C_4$-alkyl;
or a physiologically acceptable salt thereof.

2. The compound according to claim 1, wherein $R^1$ and $R^{1'}$ are each independently of the other H, cyano, methyl or methoxy.

3. The compound according to claim 1, wherein $Z^1$ is N and $Z^2$ is $CR^{1'}$.

4. The compound of formula (I) according to claim 3, wherein Q is $Ar^1$ and $Ar^1$ is phenyl which is substituted by 1 or 2 same or different radicals selected from the group consisting of halogen, cyano and $C_1$-$C_2$-haloalkyl.

5. The compound of formula (I) according to claim 3, wherein Q is a radical —C(O)—(O)$_m$—$R^2$, wherein $R^2$ is $C_1$-$C_4$-alkyl or $C_3$-$C_6$-cycloalkyl.

6. The compound of formula (I) according to claim 5, wherein $Ar^2$ is phenyl which is substituted by 1 or 2 same or different radicals selected from the group consisting of halogen, cyano, nitro, $C_1$-$C_2$-haloalkyl, $C_1$-$C_2$-haloalkoxy or $C_1$-$C_2$-haloalkylthio.

7. The compound of formula (I) according to claim 6, wherein the linker $L^1$ is of formula

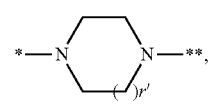
(IIa')

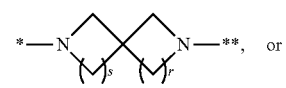
(IIa'')

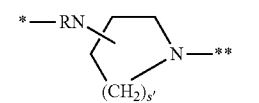
((IIb')

wherein s and r are each independently an integer 1 or 2, r' is an integer 0, 1 or 2, s' is an integer 0, 1 or 2 and R is H or methyl.

8. The compound of formula (I) according to claim 7, wherein the linker $L^2$ is a radical of formula

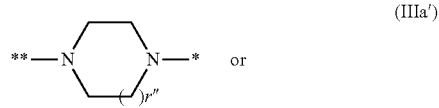
(IIIa')

-continued

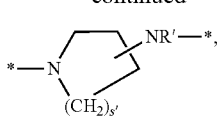
(IIIc')

wherein r" is 0 or 1, s' is an integer 1 or 2 and R' is H or methyl.

9. The compound of formula (I) according to claim 6, wherein $L^1$ is a radical

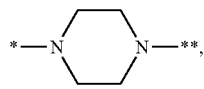

and $L^2$ is a radical

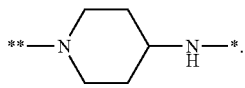

10. The compound according to claim 1 of formula

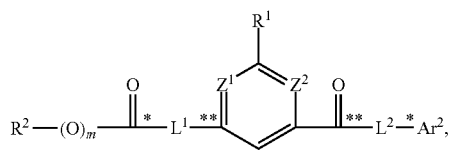
(Ia)

wherein $R^1$, $R^2$, m, $L^1$, $L^2$, $Z^1$, $Z^2$ and $Ar^2$ are each as defined in claim 1.

11. The compound according to claim 1 of formula

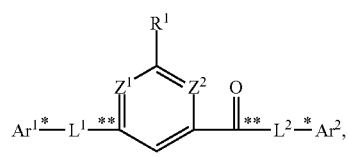
(Ib)

wherein $R^1$, $Ar^1$, $Ar^2$, $L^1$, $L^2$, $Z^1$ and $Z^2$ are each as defined in claim 1.

12. The compound according to claim 1 of formula

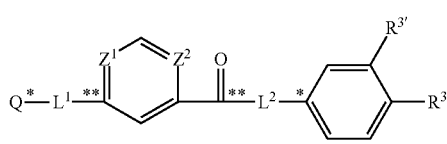
(I')

wherein Q is 4-$CF_3$-phenyl, 5-$CF_3$-pyrid-2-yl, 6-$CF_3$-pyrid-3-yl, —C(O)—O—tert-butyl or —C(O)-cyclopropyl;
$Z^1$ is N or CH;
$Z^2$ is N or CH;
$L^1$ is a radical,

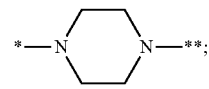

$L^2$ is a radical

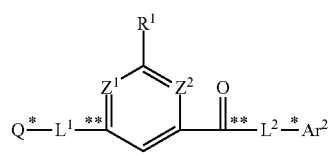

$R^3$ is $CF_3$; and $R^{3'}$ is cyano or nitro, or a physiologically acceptable salt thereof.

13. A method of controlling endoparasites, in warm-blooded animals, which comprises administering to the warm-blooded animals a veterinary effective amount of at least one compound of formula (I)

wherein $Z^1$ and $Z^2$ are each independently N or $CR^{1'}$;
$R^1$ and $R^{1'}$ are each independently of the other H, halogen, cyano, nitro, $C_1$-$C_4$-alkyl, $C_1$-$C_4$-haloalkyl, $C_1$-$C_4$-alkoxy, $C_1$-$C_3$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, halo-$C_1$-$C_4$-alkylsulfonyl, halo-$C_1$-$C_4$-alkylsulfinyl, halo-$C_1$-$C_4$-alkylsulfonylamino or benzylsulfonylamino;
Q is $Ar^1$ or —C(O)—(O)$_m$—$R^2$;
m is 0 or 1; $R^2$ is $C_1$-$C_6$-alkyl or $C_3$-$C_8$-cycloalkyl;
$Ar^1$ is (i) phenyl which is substituted by 1 to 2 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxyl, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl; or is (ii) heteroaryl selected from the group consisting of 2-, 3- or 4-pyridyl and 2- or 3-thiophenyl which is each unsubstituted or substituted by methyl, ethyl, halogen, $CF_3$ or carboxy;
$Ar^2$ is phenyl which is substituted by 1 to 3 same or different substituents selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, halo-$C_1$-$C_4$-alkylthio, $SF_5$, amino, N-mono- or N,N-di-$C_1$-$C_4$-alkylamino, aminosulfonyl, N-mono- or N,N-di-$C_1$-$C_4$-alkylaminosulfonyl, N-mono- or N,N-di-halo-$C_1$-$C_4$-alkylaminosulfonyl, $C_1$-$C_4$-alkylsulfonyl, $C_1$-$C_4$-alkylsulfinyl, $C_1$-$C_4$-alkylsulfonylamino, benzylsulfonylamino, halo-$C_1$-$C_4$-alkylsulfonyl, halo-$C_1$-$C_4$-alkylsulfinyl and halodioxolyl;

$L_1$ is a bifunctional linker radical of formula

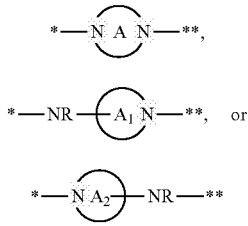

(IIa)

(IIb)

(IIc)

$L_2$ is a bifunctional linker radical of formula

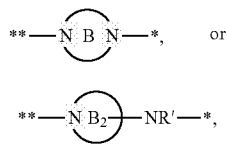

(IIIa)

or (IIIc)

A and B are each independently $C_3$-$C_8$-hetero-cycloalkylene or $C_5$-$C_{10}$-hetero-bicycloalkylene comprising two N-atoms, respectively which is each unsubstituted or substituted by $C_1$-$C_2$-alkyl;

$A_1$, $A_2$, and $B_2$ are each independently $C_3$-$C_8$-heterocycloalkylene comprising a N-atom, respectively;

R and R' are each independently of the other H or $C_1$-$C_4$-alkyl;

or a physiologically acceptable salt thereof.

14. The method according to claim 13, wherein $R^1$ and $R^{1'}$ are each independently of the other H, cyano, methyl or methoxy.

15. The method according to claim 13, wherein $Z^1$ is N and $Z^2$ is $CR^{1'}$.

16. The method according to claim 15, wherein Q is $Ar^1$ and $Ar^1$ is phenyl which is substituted by 1 or 2 same or different radicals selected from the group consisting of halogen, cyano and $C_1$-$C_2$-haloalkyl.

17. The method according to claim 15, wherein Q is a radical —C(O)—(O)$_m$—$R^2$, wherein $R^2$ is $C_1$-$C_4$-alkyl or $C_3$-$C_6$-cycloalkyl.

18. The method according to claim 17, wherein $Ar^2$ is phenyl which is substituted by 1 or 2 same or different radicals selected from the group consisting of halogen, cyano, nitro, $C_1$-$C_2$-haloalkyl, $C_1$-$C_2$-haloalkoxy or $C_1$-$C_2$-haloalkylthio.

19. The method according to claim 18, wherein the linker $L^1$ is of formula

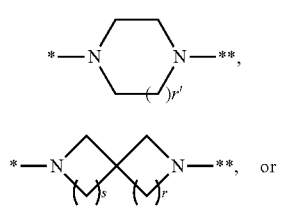

(IIa')

(IIa'')

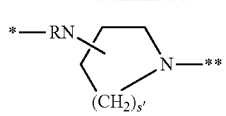

((IIb'))

wherein s and r are each independently an integer 1 or 2, r' is an integer 0, 1 or 2, s' is an integer 0, 1 or 2 and R is H or methyl.

20. The method according to claim 19, wherein the linker $L^2$ is a radical of formula

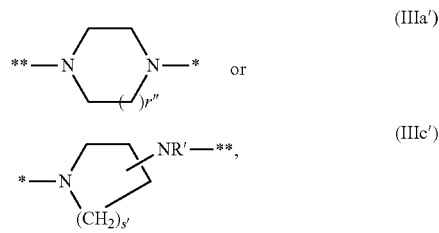

(IIIa')

or (IIIc')

wherein r" is 0 or 1, s' is an integer 1 or 2 and R' is H or methyl.

21. The method according to claim 20, wherein $L^1$ is a radical

and $L^2$ is a radical

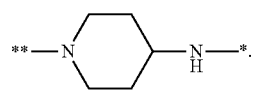

22. The method according to claim 21, wherein the at least one compound of formula (I) is a compound of formula

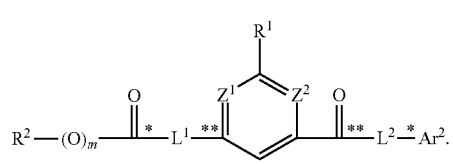

(Ia)

23. The method according to claim 13, wherein the at least one compound of formula (I) is a compound of formula

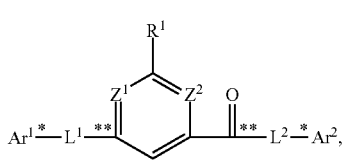

(Ib)

wherein $R^1$, $Ar^1$, $Ar^2$, $L^1$, $L^2$, $Z^1$ and $Z^2$ are each as defined in claim 13.

24. The method according to claim 13, wherein the at least one compound of formula (I) is a compound of formula
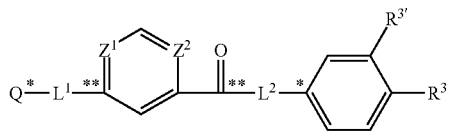 (I')
wherein Q is 4-$CF_3$-phenyl, 5-$CF_3$-pyrid-2-yl, 6-$CF_3$-pyrid-3-yl, —C(O)—O—tert-butyl or —C(O)-cyclopropyl;
$Z^1$ is N or CH;
$Z^2$ is N or CH;
$L^1$ is a radical,
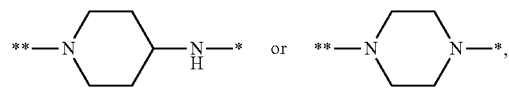
$L^2$ is a radical
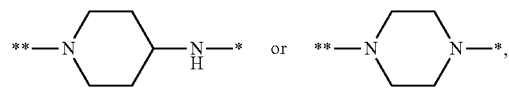
$R^3$ is $CF_3$; and $R^{3'}$ is cyano or nitro, or a physiologically acceptable salt thereof.
* * * * *

UNITED STATES PATENT AND TRADEMARK OFFICE
CERTIFICATE OF CORRECTION

PATENT NO. : 9,820,488 B2
APPLICATION NO. : 15/030476
DATED : November 21, 2017
INVENTOR(S) : Noëlle Gauvry and François Pautrat Page 1 of 1

It is certified that error appears in the above-identified patent and that said Letters Patent is hereby corrected as shown below:

In Claim 13, Column 29, Lines 13-15, after the structure " 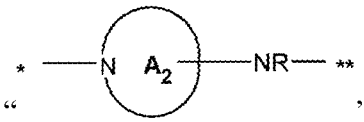 ", insert -- ; --.

In Claim 20, Column 30, Lines 19-23, delete " 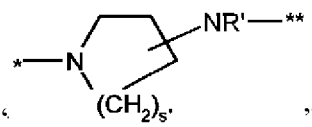 " and insert  --, therefor.

Signed and Sealed this
Twentieth Day of February, 2018

Andrei Iancu
*Director of the United States Patent and Trademark Office*